US012582530B2

(12) United States Patent
Dalla Pria et al.

(10) Patent No.: US 12,582,530 B2
(45) Date of Patent: Mar. 24, 2026

(54) IMPLANT COMPONENT

(71) Applicant: WALDEMAR LINK GMBH & CO. KG, Hamburg (DE)

(72) Inventors: Paolo Dalla Pria, Udine (IT); Angelika Harndt, Berlin (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 866 days.

(21) Appl. No.: 17/757,231

(22) PCT Filed: Dec. 15, 2020

(86) PCT No.: PCT/EP2020/086185

§ 371 (c)(1),
(2) Date: Jun. 13, 2022

(87) PCT Pub. No.: WO2021/122572

PCT Pub. Date: Jun. 24, 2021

(65) Prior Publication Data

US 2023/0000633 A1 Jan. 5, 2023

(30) Foreign Application Priority Data

Dec. 16, 2019 (EP) ..................................... 19216464

(51) Int. Cl.
*A61F 2/38* (2006.01)
*A61F 2/30* (2006.01)

(52) U.S. Cl.
CPC .. *A61F 2/3804* (2013.01); *A61F 2002/30332* (2013.01); *A61F 2002/30405* (2013.01);
(Continued)

(58) Field of Classification Search
CPC .................. A61F 2/3804; A61F 2/3859; A61F 2002/30332; A61F 2/4014; A61F 2/4059; A61F 2002/30405
See application file for complete search history.

(56) References Cited

U.S. PATENT DOCUMENTS 3,987,499 A * 10/1976 Scharbach .......... A61F 2/30767
606/247
4,878,917 A * 11/1989 Kranz ................... A61F 2/3662
623/23.45

(Continued)

FOREIGN PATENT DOCUMENTS

DE 4031520 A1 4/1992
DE 4320086 A1 12/1994

(Continued)

OTHER PUBLICATIONS

Extended European Search Report mailed Mar. 27, 2020, in connection with European Patent Application No. 19216464.8 , filed Dec. 16, 2019, 6 pgs.

(Continued)

*Primary Examiner* — Alvin J Stewart
(74) *Attorney, Agent, or Firm* — Chiesa Shahinian & Giantomasi PC

(57) ABSTRACT

A humeral implant component connectable to another humeral implant component, the humeral implant component comprising: a longitudinal axis, a first end and a second end, the first end and the second end opposing each other along the longitudinal axis of the humeral implant component, and an interface part for connecting the humeral implant component to the other humeral implant component, wherein the interface part is tapered along the longitudinal axis in a direction from the second end to the first end, the interface part being engageable with a tapered interface part of the other humeral implant component to form a tapered connection between the humeral implant component and the other humeral implant component, wherein the humeral implant component further comprises a through hole extending along the longitudinal axis for locking the tapered connection by a longitudinal fastener.

17 Claims, 12 Drawing Sheets

(52) U.S. Cl.
    CPC ............... *A61F 2002/30476* (2013.01); *A61F*
        *2002/30604* (2013.01); *A61F 2002/3822*
        (2013.01)

(56)                 References Cited

U.S. PATENT DOCUMENTS

| | | | | |
|---|---|---|---|---|
| 5,002,578 | A * | 3/1991 | Luman | A61F 2/36 |
| | | | | 623/22.46 |
| 5,906,644 | A * | 5/1999 | Powell | A61F 2/367 |
| | | | | 623/20.15 |
| 6,436,145 | B1 * | 8/2002 | Miller | A61F 2/4637 |
| | | | | 623/20.15 |
| 6,613,092 | B1 * | 9/2003 | Kana | A61F 2/30942 |
| | | | | 623/23.45 |
| 6,682,568 | B2 * | 1/2004 | Despres, III | A61F 2/30734 |
| | | | | 623/22.42 |
| 7,857,858 | B2 * | 12/2010 | Justin | A61F 2/461 |
| | | | | 623/23.46 |
| 7,998,218 | B1 * | 8/2011 | Brown | A61F 2/385 |
| | | | | 623/20.14 |
| 8,052,755 | B2 * | 11/2011 | Naidu | A61F 2/4605 |
| | | | | 623/21.12 |
| 9,427,322 | B1 * | 8/2016 | Serafin, Jr. | A61F 2/3662 |
| 2003/0204267 | A1 * | 10/2003 | Hazebrouck | A61F 2/3854 |
| | | | | 623/23.39 |
| 2004/0220673 | A1 * | 11/2004 | Pria | A61F 2/4081 |
| | | | | 623/19.12 |
| 2005/0071014 | A1 * | 3/2005 | Barnett | A61F 2/40 |
| | | | | 623/23.45 |
| 2009/0125114 | A1 * | 5/2009 | May | A61F 2/38 |
| | | | | 623/20.14 |
| 2009/0281630 | A1 * | 11/2009 | Delince | A61F 2/4081 |
| | | | | 623/19.13 |
| 2009/0281632 | A1 * | 11/2009 | Naidu | A61F 2/4637 |
| | | | | 623/20.11 |
| 2010/0241239 | A1 * | 9/2010 | Smith | A61B 17/1668 |
| | | | | 623/22.46 |
| 2014/0039633 | A1 * | 2/2014 | Roche | A61F 2/4081 |
| | | | | 623/19.13 |
| 2014/0276883 | A1 * | 9/2014 | Matyas | A61B 17/921 |
| | | | | 606/99 |
| 2014/0277524 | A1 * | 9/2014 | Brownhill | A61F 2/3804 |
| | | | | 623/20.11 |
| 2015/0081028 | A1 * | 3/2015 | Zubok | A61F 2/30734 |
| | | | | 623/20.15 |
| 2015/0094818 | A1 * | 4/2015 | Iredi | A61F 2/3859 |
| | | | | 623/18.11 |
| 2016/0030180 | A1 * | 2/2016 | Wecker | A61F 2/4014 |
| | | | | 623/18.11 |
| 2016/0128841 | A1 * | 5/2016 | Dalla Pria | A61F 2/4059 |
| | | | | 623/19.14 |
| 2016/0220378 | A1 * | 8/2016 | Bergquist | A61F 2/3804 |
| 2016/0296337 | A1 * | 10/2016 | Maale | A61F 2/40 |
| 2017/0367835 | A1 * | 12/2017 | Faccioli | A61F 2/4014 |
| 2019/0192304 | A1 * | 6/2019 | Librot | A61F 2/36 |
| 2020/0129297 | A1 * | 4/2020 | Haidukewych | A61F 2/30739 |
| 2020/0146828 | A1 * | 5/2020 | Link | A61F 2/30721 |
| 2020/0188125 | A1 * | 6/2020 | Hodorek | A61F 2/30749 |
| 2020/0214846 | A1 * | 7/2020 | Perego | A61F 2/4014 |
| 2020/0237416 | A1 * | 7/2020 | Servidio | A61F 2/28 |
| 2020/0276024 | A1 * | 9/2020 | Roberts | A61F 2/389 |
| 2021/0307919 | A1 * | 10/2021 | Paterson | A61F 2/30771 |
| 2022/0401219 | A1 * | 12/2022 | Link | A61L 27/56 |
| 2023/0157832 | A1 * | 5/2023 | Chudik | A61F 2/4014 |
| | | | | 623/19.14 |
| 2024/0082005 | A1 * | 3/2024 | Khosla | A61F 2/30749 |
| 2024/0099853 | A1 * | 3/2024 | Viscardi | A61F 2/30724 |
| 2024/0285409 | A1 * | 8/2024 | Dhamankar | A61F 2/4657 |
| 2025/0107899 | A1 * | 4/2025 | Splieth | A61F 2/4014 |
| 2025/0161058 | A1 * | 5/2025 | Goldstein | A61B 17/72 |

FOREIGN PATENT DOCUMENTS

| | | |
|---|---|---|
| DE | 10123517 C1 | 11/2002 |
| EP | 0898946 A1 | 3/1999 |
| EP | 1004283 A2 | 5/2000 |
| EP | 1824419 B1 | 4/2016 |

OTHER PUBLICATIONS

International Search Report and Written Opinion mailed Mar. 4, 2021, in connection with International Patent Application No. PCT/EP2020/086185, filed Dec. 15, 2020, 11 pgs.

Extended European Search Report mailed Nov. 8, 2023 in connection with European Patent Application No. 23188378.6, 8 pgs.

Communication pursuant to Article 94(3) EPC mailed May 27, 2025, in connection with European Patent Application No. 23188378.6, filed Jul. 28, 2023, 8 pgs.

* cited by examiner

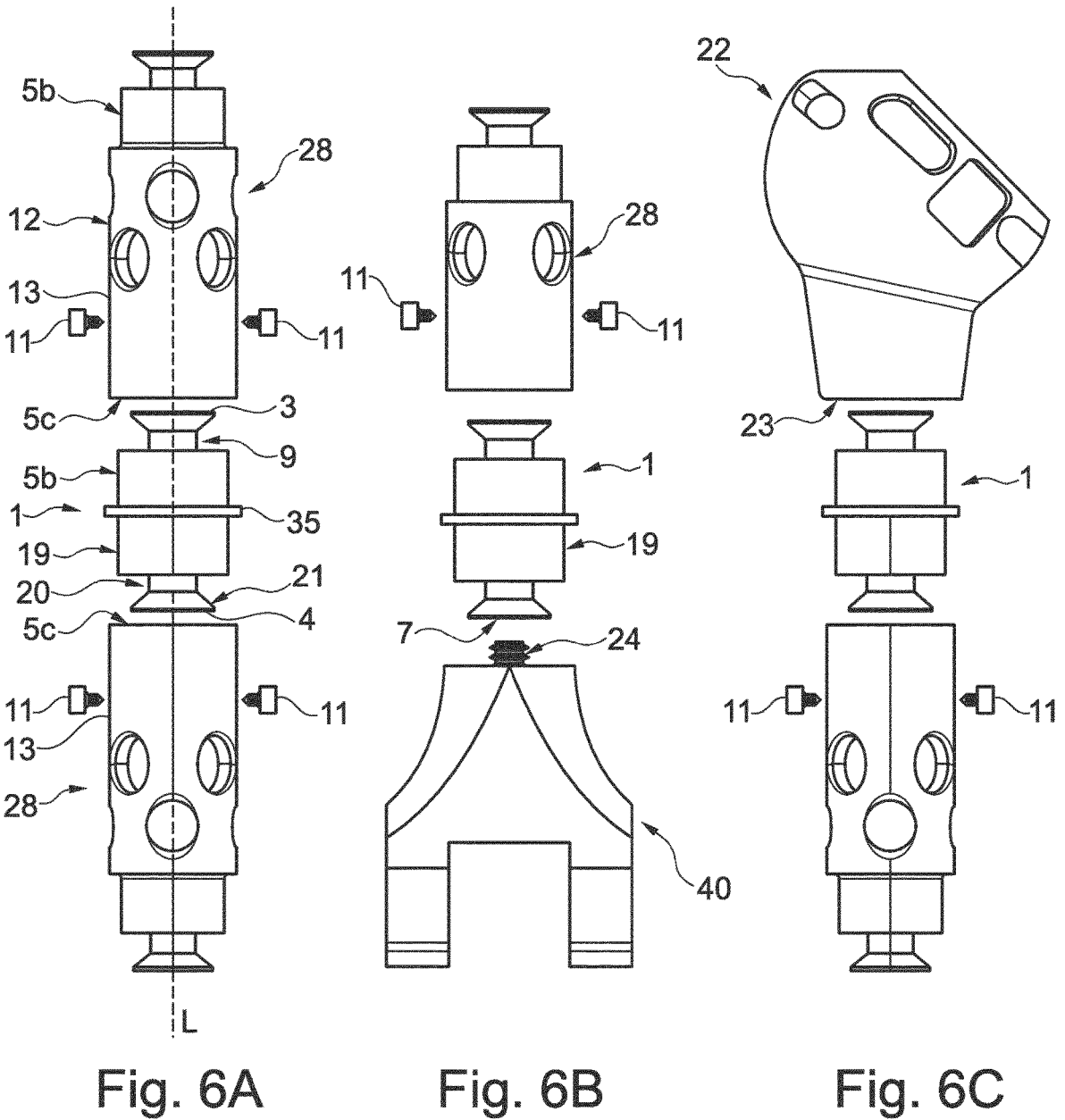
Fig. 6A          Fig. 6B          Fig. 6C

IMPLANT COMPONENT

CROSS-REFERENCE TO RELATED APPLICATIONS

This application is a national stage of International Patent Application Serial No. PCT/EP2020/086185, filed Dec. 15, 2020, which claims priority to European Patent Application No. 19216464.8, filed Dec. 16, 2019; the disclosures of all are incorporated herein by reference in their entirety.

TECHNICAL FIELD

The present disclosure relates to an implant component, preferably a humeral implant component, a set comprising one or more than one implant component, preferably humeral implant component, and a method for assembling an implant device comprising one or more than one implant component, preferably humeral implant component.

BACKGROUND OF THE INVENTION

Modular implants that can be adapted to the individual needs of a patient have been a success for replacing synovial joints. Such a replacement may become necessary due to arthritis or trauma. Further, it may be necessary to replace at least a portion of a longbone such as due to surgical removal of cancerous tissue. In other words, it may be necessary to replace a synovial joint and/or at least a portion of an adjacent longbone. Here, the modularity of implants allows highly customized joint replacements for reasonable costs although the replacement of larger amounts of tissue may still be done using customized implants, i. e. single implants that have been produced on the basis of anatomical dimensions taken from a patient. More recently, there are also modular systems for the latter cases that make the treatment of patients in need for substantial replacement of the skeleton faster and at the same time more affordable.

Nonetheless, for all these modular implants, the stability and reliability of the connection between implant components is crucial for their longevity. For this reason, a common technique to connect implant components is the use of a tapered connection. This type of connection is employed for connections that transfer compressive forces across their interfaces, is self-locking under these forces, and is based on a friction fit.

Although these tapered connections have been proven as an effective way to connect implant components to each other, issues have been observed with this type of connection that may make a replacement of implant components or even the revision of an entire implant necessary. Among these issues are unintentional loosening, fretting, wear and instability, and micromotions. It is believed that one of the reasons for these issues is an insufficient tapered connection.

Thus, it was an objective of the present disclosure to provide an interface for a tapered connection that enhances the reliability of the connection without affecting the advantage of this type of connection for modular implants.

SUMMARY OF THE INVENTION

Hence, it is an object of the present disclosure to provide an interface for a tapered connection with increased reliability and modular flexibility and a method for establishing such a tapered connection.

The above-described problems are solved by the humeral implant component according to the present disclosure.

More specifically, above-noted objectives are addressed by providing an implant component, preferably a humeral implant component, according to a first aspect, wherein the implant component is connectable to another implant component, preferably humeral implant component. The implant component comprises a longitudinal axis, a first end and a second end, the first end and the second end opposing each other along the longitudinal axis of the implant component, and an interface part for connecting the implant component to the other implant component, wherein the interface part is tapered along the longitudinal axis in a direction from the second end to the first end, the interface part being engageable with a tapered interface part of the other implant component to form a tapered connection between the implant component and the other implant component, wherein the implant component further comprises a through hole extending along the longitudinal axis for locking the tapered connection by a longitudinal fastener.

Since the implant component, preferably the humeral implant component, comprises a through hole for locking the tapered connection by the longitudinal fastener, it is possible to provide a reliable and predefined tapered connection. This is due to the tapered connection between the implant component and the other implant component, preferably humeral implant component, being tightened by the longitudinal fastener, in particular by applying a predefined torque. In order to prevent interference when establishing the predefined tapered connection, the through hole preferably does not comprise a thread. Alternatively, the through hole may include a thread with an inner diameter that is at least larger than the outer diameter of a section of the longitudinal fastener to be inserted into the through hole. With this configuration, unintentional loosening and micromotions leading to wear or fretting can be prevented.

Moreover, in conventional systems, implant components using a tapered connection are connected by forcing one implant component onto or into another implant component, in particular by means of a hammer. It turned out that this technique fails to provide a defined friction fit as it is hard to provide a predetermined compressive force during assembly. With providing an implant component comprising the through hole for locking the tapered connection by the longitudinal fastener, it is possible to apply a predefined force for locking or tightening the tapered connection between the implant components.

The implant component described herein is preferably a humeral implant component. As a result, the other implant component described herein is preferably another humeral implant component.

The implant component may be an implant component forming part of an implant device to be implanted into a patient, such as an upper limb implant device.

The expression "implant device" may generally refer to an assembly of at least two implant components being connected to each other by tapered connections, preferably by the tapered connections as described in the present disclosure.

The longitudinal axis of the implant component may be a central axis passing through the longest extension of the implant component. The longitudinal axis may also be a symmetry axis, such as the rotational axis in case the implant component has a rotational symmetry. The longitudinal axis may also run through the center of the area of each cross-section along the longest extension of an implant component.

The interface part may generally be the part of the implant component which establishes the connection between the implant component and the other implant component.

The interface part is tapered along the longitudinal axis. For example, the interface part may comprise a slanted element having the shape of a cone or truncated cone. The longitudinal axis may pass through the cone apex or through the center of the truncated cone. In this case, the tapering of the interface part may be defined by the full angle of the cone (opening angle of the cone). For example, the full angle may be in the range from 1° to 20°, preferably from 1° to 10°, more preferably from 1° to 6°, even more preferably from 1° to 5°, most preferably from 1° to 4°, and in particular from 1° to 3°. The full angle may also be 2° 52' (conicity 1:20) or 5° 43'30" (conicity 1:10).

The tapered connection between the implant component and the other implant component may be established by a frictional engagement due to the static friction between the two components, i.e. between the tapered interface part of the implant component and the tapered interface part of the other implant component.

The through hole is preferably formed through the entire extension of the implant component from the first end to the second end.

The longitudinal fastener is preferably a screw.

The implant component and/or the other implant components described in this disclosure are made of biocompatible materials and in particular metal and metal alloys. In particular, the implant component and/or the other implant component described in this disclosure may be entirely or partly made of commercially pure Titanium and/or $Ti_6Al_4V$ (or other Ti-alloys) and/or CoCr (wherein the term "CoCr" shall mean the general term for different alloys commonly used for orthopedic implants) and/or Polyethylene.

According to an embodiment, the through hole comprises a thread for a threaded engagement with the longitudinal fastener. Accordingly, the longitudinal fastener used in this embodiment is a screw.

With this configuration, it is possible to provide a simple engagement mechanism between the through hole of the implant component and the longitudinal fastener. In addition, it is possible to apply a predefined force for tightening or locking the tapered connection by screwing the longitudinal fastener up to a predetermined torque value.

According to an embodiment, the interface part is one of an inner interface part and an outer interface part.

The inner interface part may be a recess formed within the implant component. The outer interface part may constitute a part of the outer shape of the implant component. In particular in case the implant component comprises a substantially rotationally symmetric shape, the inner interface part has a surface, wherein the surface normal vector is directed radially inwards, i.e. pointing in a direction towards the longitudinal axis of the implant component. Accordingly, an outer interface part has a surface, wherein the surface normal vector is directed radially outwards, i.e. pointing in a direction away from the longitudinal axis of the implant component. In other words, the latter surface normal vector points in a direction substantially opposite to the direction of the surface normal vector of the inner interface part.

In general, the inner interface part of one implant component may form a tapered connection with the outer interface part of another implant component, and vice versa.

With this configuration, modular flexibility of the implant component can be increased since the interface part can be either an inner interface part or an outer interface part.

According to an embodiment, the inner interface part is provided at the second end and the outer interface part is provided at the first end.

For example, in case the implant component comprises an elongated body, the inner interface part may be provided at one end of the elongated body and the outer interface part may be provided at the other end of the elongated body.

Further, the inner interface part and the outer interface part preferably overlap along the longitudinal axis. In other words, the inner interface part is at least partly surrounded by the outer interface part.

With this configuration, having an implant component comprising an inner interface part at the second end and another implant component comprising an outer interface part at the first end, wherein the inner interface part of the implant component and the outer interface part of the other implant component may form the tapered connection, it is possible to provide a combined implant component having a different shape than the implant component or the other implant component, thereby increasing modular flexibility.

According to an embodiment, the implant component further comprises another interface part for connecting the implant component to yet another implant component via another tapered connection, wherein the other interface part is the other one of the inner interface part and the outer interface part.

The yet another implant component described herein is preferably yet another humeral implant component.

For example, in case the implant component comprises an elongated body, the implant component may comprise both the inner interface part and the outer interface part, wherein the inner interface part may be provided at one end of the elongated body and the outer interface part may be provided at the other end of the elongated body.

With this configuration, it is possible to provide an implant component that has two interface parts and thus can be connected, via tapered connections, with two other implant components, thereby even further increasing modular flexibility of the implant component.

According to an embodiment, the implant component further comprises a circumferential groove comprising a tapered groove side wall, wherein the tapered groove side wall is tapered along the longitudinal axis in a direction from the first end to the second end. The tapered groove side wall is engageable with at least one transversal fastener, preferably at least two transversal fasteners, for locking the other tapered connection.

The tapered groove side wall is tapered along the longitudinal axis. For example, the tapered groove side wall may comprise a slanted element having the shape of a cone or truncated cone. The longitudinal axis may pass through the cone apex or through the center of the truncated cone. In this case, the tapering of the tapered groove side wall may be defined by an inclination angle between the slanted element of the tapered groove side wall and the longitudinal axis. For example, the inclination angle may be in the range from 1° to 89°, preferably from 15° to 60°, more preferably from 20° to 55°, even more preferably from 30° to 50°, most preferably from 42° to 47°, and in particular 45°. Generally, the larger the inclination angle, the higher are the compressive forces that can be applied when fastening the transversal fastener using a fixed torque.

The transversal fastener is preferably a screw and more preferably a stud screw. If being a screw, the transversal fastener preferably has a chamfered tip, wherein the chamfered tip even more preferably corresponds to the inclination angle of above-noted tapered sidewall. The tip may also be curved or have a round shape. The transversal fastener has a longitudinal axis and preferably engages the tapered groove side wall such that the longitudinal axis of the transversal fastener and the longitudinal axis of the implant component are substantially perpendicular to each other.

The tip of the transversal fastener may engage with the tapered groove side wall in such a way that a preload is generated in the tapered connection, i.e. the other tapered connection according to the embodiment. According to the principle of the inclined plane, the tip of the transversal fastener may generate a preload in the tapered connection by moving into the direction of the longitudinal axis of the transversal fastener (usually by turning the transversal fastener) and interacting with the tapered groove side wall, thereby locking the two implant components forming the other tapered connection according to the embodiment and thus preventing relative movement of the two implant components. In other words, the movement of the transversal fastener along its longitudinal axis during fastening is converted into a movement along the longitudinal axis of the tapered connection due to the inclination of the tapered groove side wall in relation to these axes.

The other groove side wall, i.e. the groove side wall opposite to aforementioned tapered groove side wall, may not be tapered. In particular, the other groove side wall may well have a surface extending substantially perpendicularly to the longitudinal axis of the implant component.

In an example, the circumferential groove and the interface part of the implant component may be provided at the first end of the implant component, wherein the circumferential groove may be located closer to the first end than the interface part. The implant component may form a tapered connection with the other implant component by relatively moving the implant component towards the other implant component in a direction from the second end to the first end. In the example, the tapered interface part of the other implant component may define a recess in the other implant component and the interface part of the implant component may have an outer shape of a truncated cone. Hence, the tapered connection is formed by inserting the implant component into the other implant component.

After having established the tapered connection, i.e. the other tapered connection according to the embodiment, the tapered connection may be locked by engaging the tapered groove side wall of the implant component with at least one transversal fastener. Since the circumferential groove is tapered in the opposite direction or in the opposite way in relation to the interface part and is located closer to the first end than the interface part, engaging the tapered groove side wall with the transversal fastener causes the implant component to be pulled further into the other implant component.

With this configuration, it is possible to provide a more reliable tapered connection. This is due to the tapered connection between the implant component and the other implant component being tightened by the transversal fastener. With this configuration, unintentional loosening and micromotions leading to fretting, wear and/or instability can be prevented.

Moreover, with this configuration, it is possible to provide an implant component, i.e. one single implant component, that has two interface parts (in particular at opposite ends along its longitudinal axis) and, thus, can be connected, via two tapered connections, with two other implant components, wherein each of the two tapered connections can be locked and thereby secured individually. One of the two tapered connections may be locked by the longitudinal fastener, whereas the other one of the two tapered connections may be locked by the at least one transversal fastener. In other words, both the longitudinal fastener and the transversal fastener interact with the same implant component (but at different interface parts) in order to lock the two tapered connections with the two other implant components. Hence, the implant component according to the embodiment not only provides for a higher modularity, but also for a more reliable tapered connection with each of the other implant components.

Further, it is possible to apply a defined force for locking or tightening the tapered connection between the implant components by applying a predetermined torque to the transversal fastener.

Moreover, in the example described above, the tapered connection is locked even more reliably since the implant component is pulled into the other implant component and pulling the interface part into the recess of the other interface part results in a better alignment than pushing it.

In a preferred embodiment, at least two of the transversal fastener are provided, wherein the transversal fasteners are provided at equal intervals in the circumferential direction of the circumferential groove. For example, in case two transversal fasteners are provided, the two transversal fasteners may be arranged at an angle of 180° in the circumferential direction of the circumferential groove (i. e. on opposite sides) such that the two transversal fasteners have the same longitudinal axis and are arranged opposite to each other. This allows for a controlled and reliable locking of the tapered connection, i.e. the other tapered connection according to the embodiment.

In a preferred embodiment, the tapered groove side wall is preferably integrally formed with the implant component. In other words, the tapered groove side wall is an integral part of the implant component. With this configuration, not only less pieces need to be handled during assembly and surgery, it is also possible to fasten and lock the tapered connection, i.e. the other tapered connection according to the embodiment, by means of the transversal fastener more reliably without the danger that upon interaction between the transversal fastener and the tapered groove side wall the configuration of the circumferential groove is modified. Further, stress concentrations are avoided as well as a wrong assembly or an unintended loosening that may occur with a section having the tapered groove side wall being modularly configured. Accordingly, a mechanically safer configuration of the implant component and, hence, a mechanically safer tapered connection can be provided.

According to an embodiment, the implant component further comprises an elongated body, the elongated body being positioned between the first end and the second end, wherein the elongated body comprises at least one, preferably at least two transversal holes for being penetrated by the transversal fastener for locking the other tapered connection.

Preferably, the elongated body is a cylindrical body. Even more preferably, the elongated body is at least partly hollow.

The elongated body may be provided as a modular component with a variety of lengths.

The elongated body may be connected, preferably integrally connected, with the interface part of the implant component, i. e. it forms a part of the implant component's body. In an example, the elongated body may be located at one of the first end and the second end and the interface part may be located at the other one of the first end and the second end.

In particular in case of a cylindrical shape of the elongated body, the at least two transversal holes may be provided at equal intervals in the circumferential direction of the elongated body or opposite to each other.

With this configuration, it is possible to provide an additional or alternative shape of the implant component that results in the advantages of the implant components described above. This results in the modular flexibility of the tapered connection and the implant component being enhanced.

In an example, the elongated body may comprise at least one hole, in particular for receiving medicine. It is also conceivable that the at least one hole may be provided for attaching soft tissue thereto using sutures.

According to an embodiment, the implant component further comprises a plate-shaped portion, the plate-shaped portion being attached to, preferably integrally formed with, the second end and extending away from the second end parallel to the longitudinal axis in a direction from the first to the second end, wherein the plate shaped portion comprises at least one, preferably at least two transversal through holes for being penetrated by fixation means.

In an example, the fixation means may be cortical screws.

By implementing this configuration, it is possible to provide yet another alternative shape of the implant component showing the advantages described in relation to the previously described implant components. Accordingly, the modular flexibility of the tapered connection and the implant component is further increased.

According to an embodiment, the interface part forms a conical taper, preferably a Morse taper, and/or the other interface part forms a conical taper, preferably a Morse taper.

The conical taper may have the shape of a cone or a truncated cone comprising a full angle, in particular in the ranges defined above.

According to an embodiment, the implant component further comprises a second interface part for connecting the implant component to the other implant component, wherein the second interface part is tapered along the longitudinal axis in a direction from the first end to the second end, the second interface part being engageable with the tapered interface part of the other implant component to form the tapered connection between the implant component and the other implant component.

The second interface part may be the same or may have the same features as the interface part described above, with the exception that the second interface part is tapered in the opposite direction compared to the interface part described above.

For example, the interface part may be provided at the first end of the implant component and the second interface part may be provided at the second end of the implant component. The interface part and the second interface part may be integrally formed.

With this configuration, it is possible to provide an implant component constituting an adapter having the same ends since the second interface part is tapered in the opposite direction compared to the interface part described above. In an example, the adapter may be a male-male adapter.

According to an embodiment, the implant component further comprises a second circumferential groove comprising a second tapered groove side wall, wherein the second tapered groove side wall is tapered along the longitudinal axis in a direction from the second end to the first end, wherein the second tapered groove side wall is engageable with at least one transversal fastener, preferably at least two transversal fasteners, for locking the tapered connection.

The second circumferential groove and the second tapered groove side wall may be the same or may have the same features as the circumferential groove and the tapered groove side wall described above, with the exception that the second tapered groove side wall is tapered in the opposite direction compared to the tapered groove side wall described above.

In an example, the configuration of the implant component as seen along the longitudinal axis from the second end to the first end may be as follows: second tapered groove side wall, second circumferential groove, second interface part, interface part, circumferential groove, tapered groove side wall.

With this configuration, it is possible to provide, for example, a male-male adapter additionally having the advantages as described above in context with the circumferential groove of the implant component.

According to a second aspect, the present disclosure provides a set. The set comprises the implant component according to the first embodiment described above, a second implant component, wherein the second implant component comprises a tapered interface part at one end thereof, wherein the interface part of the implant component is configured to engage with the tapered interface part of the second implant component to form a tapered connection between the implant component and the second implant component, and a screw, the screw being provided in the second implant component, wherein the screw is arranged to lock the tapered connection by forming a threaded engagement with the through hole of the implant component.

The second implant component described herein is preferably a second humeral implant component.

The second implant component may be a humeral implant body. Since the screw is provided in the second implant component, it preferably rests on a screw seat of the second implant component in the state of locking the tapered connection.

The screw may be a captive or retentive screw. The second implant component may comprise a recess in which the tapered interface part is provided. In this case, the tapered interface part of the second implant component may constitute an inner tapered interface part. In an example, the tapered interface part may be a conical taper, in particular a Morse taper, wherein the screw is provided in the second implant component such that a longitudinal screw axis coincides with a longitudinal taper axis of the tapered interface part of the second implant component. In case of a captive screw, the captive screw may penetrate through a ring-shaped body, wherein the ring-shaped body may comprise an outer thread. The outer thread of the ring-shaped body may engage an inner thread provided in the recess of the second implant component. Accordingly, the ring-shaped body may be fixed in the second implant component by forming a threaded engagement with the inner thread of second implant component, thereby fixing the captive screw within the second implant component.

With this configuration, it is possible to provide a reliable tapered connection between the implant component and the second implant component and having the same advantages as described above.

According to a third aspect, a set is disclosed that comprises the implant component according to the first embodiment described above, a second implant component, wherein the second implant component comprises a tapered interface part at one end thereof, wherein the interface part of the implant component is configured to engage with the tapered interface part of the second implant component to form a tapered connection between the implant component and the second implant component. The second implant component further comprises a threaded hole extending from the one end of the second implant component into the second implant component, and a screw, wherein the screw is configured to penetrate the through hole of the implant component and to lock the tapered connection by engaging the threaded hole.

The threaded hole may be a bore hole drilled into the second implant component and provided with an inner thread.

The screw may generally be sized to penetrate the entire through hole of the implant component and to penetrate the threaded hole of the second implant component.

In a preferred example, the screw may not engage with the through hole of the implant component. For this purpose, the screw may comprise the thread only at the end of the screw penetrating into the threaded hole of the second implant component. Additionally, or alternatively, the through hole of the implant component may not comprise a thread.

With this configuration, it is possible to combine the implant component with the second implant component via a reliable tapered connection having the same advantages as described above.

According to a fourth aspect, a set is disclosed, wherein the set comprises the implant component according to the first embodiment described above, a second implant component, wherein the second implant component comprises a second implant component tapered interface part at one end thereof, wherein the interface part of the implant component is configured to engage with the second implant component tapered interface part to form a second implant component tapered connection between the implant component and the second implant component, the second implant component further comprising a threaded hole extending from the one end of the second implant component into the second implant component, a third implant component, wherein the third implant component comprises a third implant component tapered interface part at one end thereof, wherein the other interface part of the implant component is configured to engage with the third implant component tapered interface part to form a third implant component tapered connection between the implant component and the third implant component, and a screw, the screw being provided in the third implant component, wherein the screw is configured to lock the third implant component tapered connection and the second implant component tapered connection by forming a threaded engagement with the threaded hole of the second implant component.

The third implant component described herein is preferably a third humeral implant component.

The second implant component tapered interface part may be the same or may have the same features as the tapered interface part described above. The second implant component tapered connection may be the same or may have the same features as the tapered connection described above. The third implant component tapered interface part may be the same or may have the same features as the tapered interface part described above. The third implant component tapered connection may be the same or may have the same features as the tapered connection described above.

The third implant component may be a humeral implant body.

The screw may be the same or may have the same features as the captive or retentive screw described above, with the exception that the screw may be configured not to engage with the through hole of the implant component.

With this configuration, it is possible to provide two reliable tapered connections with only one screw, thereby reducing the number of components and increasing ease of assembly.

According to an embodiment, the screw comprises a first thread and a second thread, the first thread being different from the second thread, wherein the first thread and the second thread are arranged separately along a longitudinal screw axis of the screw, wherein the first thread is configured to form a threaded engagement with the through hole of the implant component and the second thread is configured to form a threaded engagement with the threaded hole of the second implant component.

For example, the first thread may be provided closer to a screw head than the second thread. For example, the second thread may be smaller in diameter than the first thread. In particular, the second thread may be 1 to 2 mm smaller than the first thread. In an example, the first thread may be a M6-thread and the second thread may be a M5-thread.

The second thread may be sized to penetrate the through hole of the implant component without engaging the through hole of the implant component.

With this configuration, it is possible to establish two threaded connections with only one screw, thereby reducing the number of components and increasing ease of assembly.

According to an embodiment, the implant component is a first implant component, wherein the set of this embodiment further comprises in addition to the first and second implant components: a third implant component, the third implant component being an implant component according to the first embodiment described above, the third implant component forming another tapered connection with the other interface part of the first implant component, and at least one, preferably at least two transversal fasteners, the transversal fastener being configured to penetrate the at least one, preferably at least two transversal holes of the third implant component for locking the other tapered connection by engaging with the tapered groove side wall of the first implant component.

The first implant component described herein is preferably a first humeral implant component.

The transversal fastener may be the same or may have the same features as the transversal fastener described above.

With this configuration, it is possible to provide an implant device being composed of several implant components, wherein the implant components are connected by reliable tapered connections having the same advantages as described above.

According to a fifth aspect, yet another set is disclosed, wherein the set comprises at least two of the implant components according to the first embodiment described above, wherein one of the implant components is configured to form a tapered connection with the other one of the implant components, and wherein the tapered connection is locked by the at least one, preferably at least two transversal fasteners.

In an example, the one of the implant components may be the implant component comprising the elongated body and the other one of the implant components may also be the implant component comprising the elongated body.

As described above, the elongated body may be provided with a variety of lengths.

With this configuration, it is possible to provide an implant device having an adapted, customized length and having a reliable tapered connection with the same advantages as described above.

According to a sixth aspect, it is further disclosed a set comprising two of the sets according to the third aspect described above, a third implant component, the third implant component comprising a longitudinal axis, a first end and a second end, the first end and the second end opposing each other along the longitudinal axis of the third implant component, a first end tapered interface part and a second end tapered interface part, the first end tapered interface part being located at the first end and the second end tapered interface part being located at the second end of the third implant component, wherein the first end tapered interface part is tapered along the longitudinal axis of the third implant component in a direction from the first to the second end of the third implant component and the second end tapered interface part is tapered in a direction opposite to the first end tapered interface part, at least one, preferably at least two transversal holes, arranged between the first end and the second end of the third implant component, non-equidistant from the first and the second end of the third implant component, at least one, preferably at least two transversal fasteners configured to penetrate the transversal holes, wherein one of the two sets is configured to form a tapered connection at the first end of the third implant component and the other one of the two sets is configured to form a tapered connection at the second end of the third implant component, wherein one of the first and second ends of the implant components of the two sets face each other and the other one of the first and second ends of the implant components of the two sets face away from each other when forming tapered connections with the third implant component, wherein the tapered connections are locked by the transversal fastener engaging with the respective tapered groove side wall of the implant components.

The third implant component may comprise an elongated body and may comprise a cylindrical shape. In this case, the longitudinal axis may pass through the center of the cylindrical shape.

The third implant component may be a diaphyseal segment. In such an embodiment, the diaphyseal segment replaces, for example, at least a section of a fractured or cut long bone. Due to the above-described configuration of the interface part, a surgeon is able to first anchor the implant stems within the bone tissue of the long bones before alignment of the bones. The latter is done upon final assembly of the diaphyseal segment. This procedure of anchoring, alignment, and assembly enhances the implantation of such a segment.

The first end tapered interface part and the second end tapered interface part may be the same or may have the same features as the tapered interface part of the other implant component described above. The first end tapered interface part and the second end tapered interface part may each be an inner interface part. In this case, the third implant component may constitute a female-female adapter, wherein each end of the female-female adapter may receive the implant component of the set according to the third embodiment described above to form a respective tapered connection between the respective implant component of the set and the third implant component.

The third implant component may comprise at least two transversal holes. In the case of a cylindrical shape of the third implant component, the at least two transversal holes may be arranged such that one of the two transversal holes may be located closer to the first end than the other of the two transversal holes, while the other of the two transversal holes may be located closer to the second end than the one of the two transversal holes. In particular, the two transversal holes may be arranged such that, when being inserted in the third implant component, the implant component of the respective set may be locked by the transversal fastener penetrating through the transversal holes.

The third implant component may comprise more than two transversal holes, for example, four or six transversal holes. In this case, two of the four transversal holes and, respectively, three of the six transversal holes, may be located closer to one of the first and second end of the third implant component than the remaining two and, respectively, remaining three transversal holes. The two and, respectively, the three transversal holes may have the same distance from the respective first or second end of the third implant component and may be arranged at equal intervals in the circumferential direction of the third implant component.

When forming tapered connections with the third implant component, the two sets according to the third embodiment may be arranged with respect to each other such that the first end of the one of the two sets may face the first end of the other of the two sets. In this case, the second end of the one of the two sets may face away from the second end of the other of the two sets.

With this configuration, it is possible to provide an implant device which, for example, can be applied to the humerus of a human being, the implant device having the same advantages as regards the tapered connection as described above.

According to a seventh aspect of the claimed invention, a method for assembling an implant device is disclosed. The implant device comprises one or more than one of the implant components according to the first aspect described above and/or one or more than one of the set according to any one of the second to sixth aspects described above. The method comprises the steps of:

i) forming at least one tapered connection by engaging an interface part with one of another interface part and a tapered interface part,
  ii) locking the at least one tapered connection by means of the longitudinal fastener and/or the screw and/or the at least one, preferably at least two transversal fasteners.

The tapered connection may be the same or may have the same features as the tapered connection described above.

The step of forming the at least one tapered connection may comprise pre-arranging the implant components such that the longitudinal axis of one implant component may substantially coincide with the longitudinal axis of another implant component. In other words, the two implant components may be linearly pre-arranged one after another.

The step of forming the at least one tapered connection may comprise moving one of the implant components towards the other of the implant components, with the interface part of the one of the implant components being directed towards the tapered interface part or the other interface part of the other of the implant components.

The step of locking the at least one tapered connection may comprise locking the tapered connection by means of the longitudinal fastener or the at least one, preferably at least two transversal fasteners. Alternatively, the step of locking the at least one tapered connection may comprise locking the tapered connection by means of the longitudinal fastener and, additionally, by means of the at least one, preferably at least two transversal fasteners, thereby establishing an even more reliable tapered connection.

With this method, it is possible to assemble an implant device comprising several implant components or sets of the implant components in a reliable manner, i.e. preventing unintentional loosening and fretting due to micromotions. Furthermore, with this method, it is possible to achieve a defined friction fit between the implant components.

Further embodiments of the present disclosure may be found in the following description of particular embodiments referring to the accompanying drawings.

BRIEF DESCRIPTION OF THE DRAWINGS

FIG. 6A is a front view of a set, comprising the humeral implant component of FIG. 1 comprising a second interface part and a second circumferential groove, in an un-assembled state.

FIG. 6B is a front view of another set, comprising the humeral implant component of FIG. 6A, in an un-assembled state.

FIG. 6C is a front view of yet another set, comprising the humeral implant component of FIG. 6A, in an un-assembled state.

DETAILED DESCRIPTION OF PREFERRED EMBODIMENTS

Figures 1, 2A, 2B:
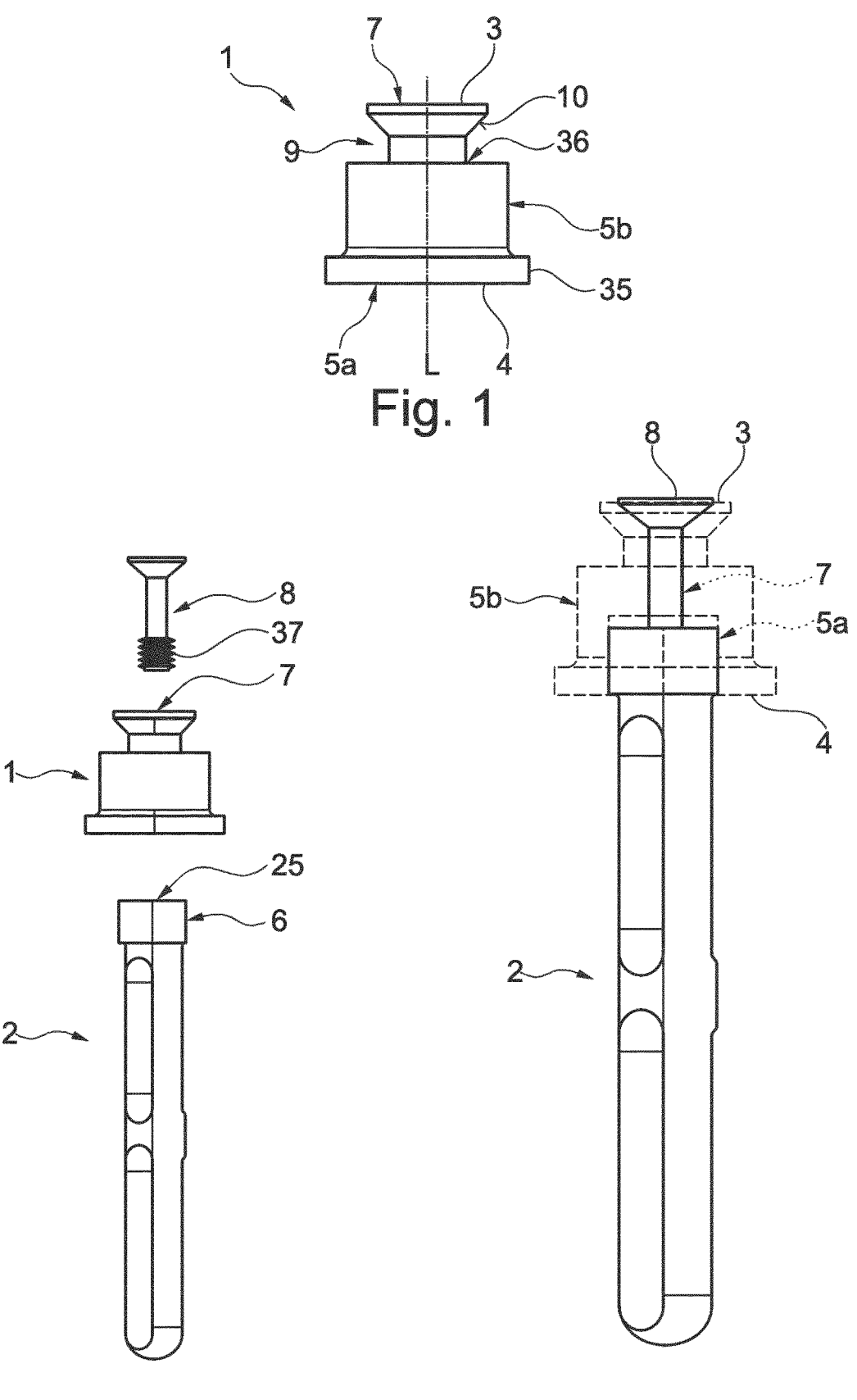
FIG. 1 is a front view of a humeral implant component.
FIG. 2A is a front view of a set, comprising the humeral implant component of FIG. 1, a longitudinal fastener, and another humeral implant component, in an un-assembled state.
FIG. 2B shows the set of FIG. 2A in an assembled state.

Hereinafter, embodiments according to the disclosure will be described in detail with reference to the accompanying drawings in order to describe the disclosure using illustrative examples. Further modifications of certain individual features described in this context can be combined with other features of the described embodiments to form further embodiments of the disclosure.

Throughout the drawings, the same reference numerals are used for the same elements.

FIG. 1 is a front view of the humeral implant component 1 of the present disclosure. The humeral implant component 1 comprises a longitudinal axis L. The humeral implant component 1 comprises a rotationally symmetric shape, wherein the rotational axis coincides with the longitudinal axis L. The humeral implant component 1 comprises a first end 3 and a second end 4 opposing each other along the longitudinal axis L. The humeral implant component 1 comprises, in the order from the first end 3 to the second end 4 along the longitudinal axis 3: a tapered groove side wall 10, a circumferential groove 9, an interface part 5*b*, and a base part 35.

The interface part 5*b* has the shape of a conical taper and is tapered in a direction from the second end 4 to the first end 3 along the longitudinal axis L. The circumferential groove 9 is located closer to the first end 3 than the interface part 5*b*. The circumferential groove 9 is formed by the tapered groove side wall 10 and another groove side wall 36. The other groove side wall 36 comprises a flat surface substantially perpendicular to the longitudinal axis L of the humeral implant component 1. The tapered groove side wall 10 is tapered in a direction from the first end 3 to the second end 4 along the longitudinal axis L. The tapered groove side wall 10 is formed integrally with the humeral implant component 1.

The humeral implant component 1 further comprises a through hole 7 and an interface part 5*a*, which is an inner interface part 5*a*. The inner interface part 5*a* has the shape of a conical taper and is provided at the second end 4 of the humeral implant component 1. In other words, the inner interface part 5*a* is formed in a recess of the humeral implant component 1. The through hole 7 and the inner interface part 5*a* can be better seen in FIG. 2B. The through hole 7 of this embodiment is preferably not threaded.

FIG. 2A is a front view of a set comprising the humeral implant component 1 of FIG. 1, a longitudinal fastener 8 and another humeral implant component 2 in an un-assembled state. The longitudinal fastener 8 is preferably a screw comprising a screw head at one end thereof and a thread 37 at the other end thereof. The other humeral implant component 2 is a stem 2. The stem 2 may be applied to a bone of a human being. The other humeral implant component 2 comprises at one end thereof facing the humeral implant component 1 a tapered interface part 6 which is configured to engage with the inner interface part 5*a* of the humeral implant component 1 to form a tapered connection. In this case, the tapered interface part 6 can be considered as an outer interface part. For locking the tapered connection between the humeral implant component 1 and the other humeral implant component 2, the other humeral implant component 2 comprises, at the end where the tapered interface part 6 is provided, a threaded hole 25. The threaded hole 25 forms a recess axially extending into the other humeral implant component 2. The thread of the threaded hole 25 is configured to engage with the thread 37 of the screw 8.

FIG. 2B shows the set of FIG. 2A in an assembled state. As can be seen, the screw 8 penetrates through the through hole 7 of the humeral implant component 1 such that the thread 37 of the screw 8 is an engagement with the threaded hole 25 of the other humeral implant component 2, thereby locking the tapered connection between the humeral implant component 1 and the other humeral implant component 2.

Further, FIG. 2B illustrates that the inner interface part 5a and the outer interface part 5b of the humeral implant component 1 preferably overlap along the longitudinal axis L. In other words, the inner interface part 5a is surrounded by the outer interface part 5b (at least partially) along the longitudinal axis.

This allows for a compact assembly since the humeral implant component 1 may serve as an adapter between implant components of different diameters without significantly increasing the size of the assembly.

Figure 10:
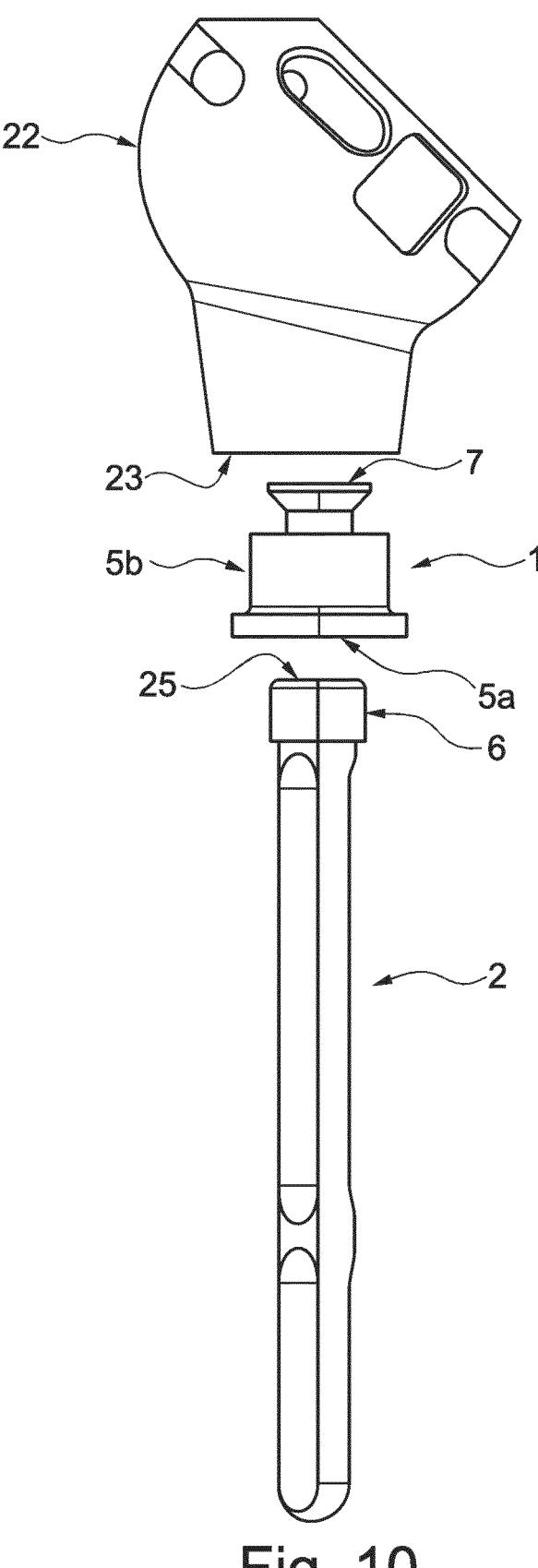
FIG. 10 is a front view of a set, comprising the humeral implant component of FIG. 1, the second humeral implant component of FIG. 7, and the other humeral implant component of FIG. 2A, in an un-assembled state.

For example, the humeral implant component 1 in FIG. 2 acting as an adapter allows for combining a stem 2 for implantation into a cavity of a humerus and a humeral implant component with a larger cross-section, such as a partial replacement of a humerus (cf. humeral implant component 28 of FIG. 4 or humeral implant component 29 of FIG. 12) or a joint replacement (cf. humeral implant component 22 of FIG. 10). Accordingly, this overlapping configuration of the inner interface part 5a and the outer interface part 5b enhances the modular flexibility.

Figures 3A, 3B:
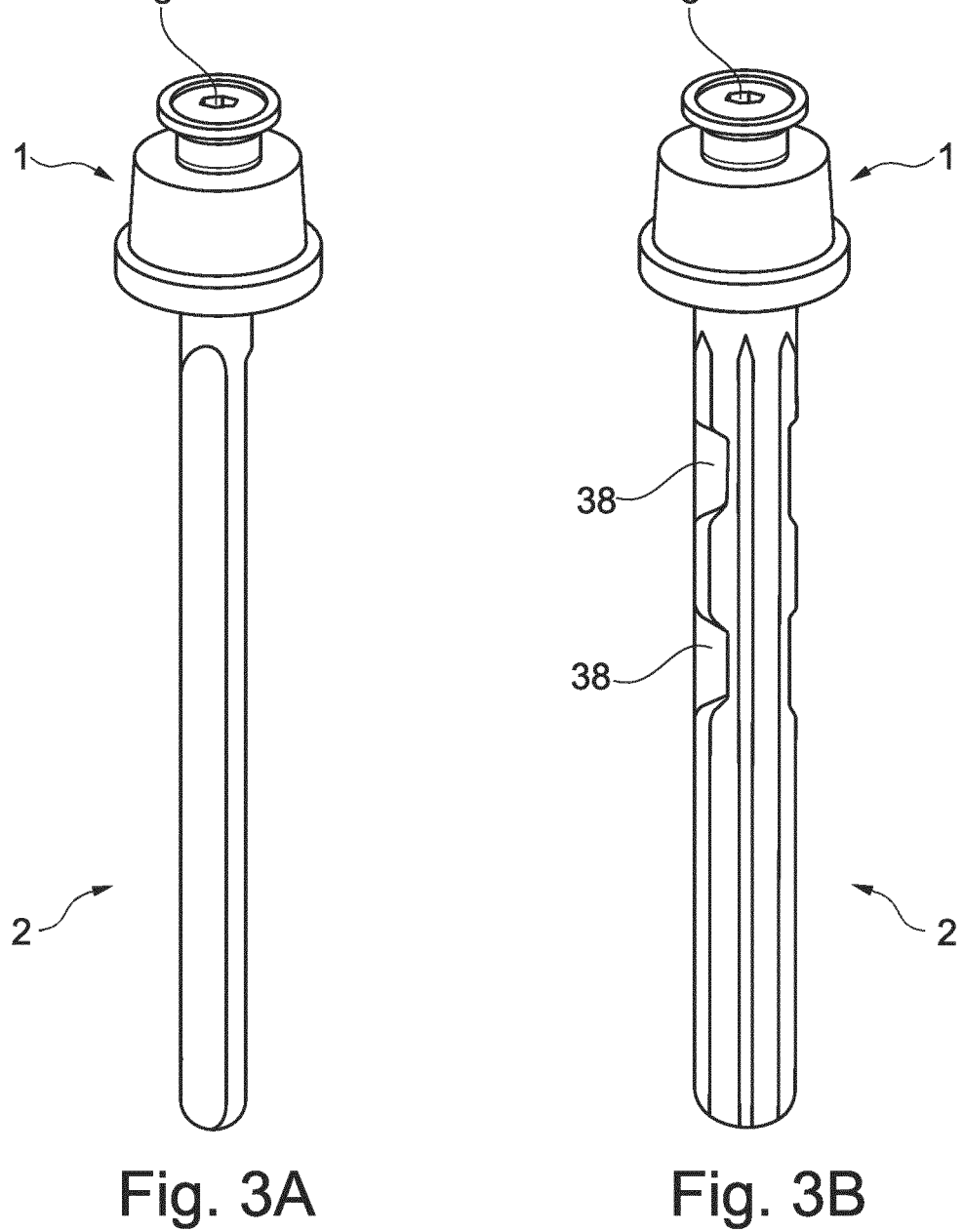
FIG. 3A is a perspective view of the humeral implant component of FIG. 1 forming a tapered connection with another humeral implant component.
FIG. 3B is a perspective view of the humeral implant component of FIG. 1 forming a tapered connection with another humeral implant component.

FIG. 3A is a perspective view of the humeral implant component 1 of FIG. 1 forming a tapered connection with the other humeral implant component 2. FIG. 3B is a perspective view of the humeral implant component 1 of FIG. 1 forming a tapered connection with another humeral implant component 2. In FIG. 3B, the stem 2 additionally comprises two stem holes configured to be penetrated by fixation means 16 for fixation of the stem 2 in a bone of a human being. As can be seen, the screw 8 is preferably a countersunk screw, the head of which penetrates into the humeral implant component 1.

Figure 4:
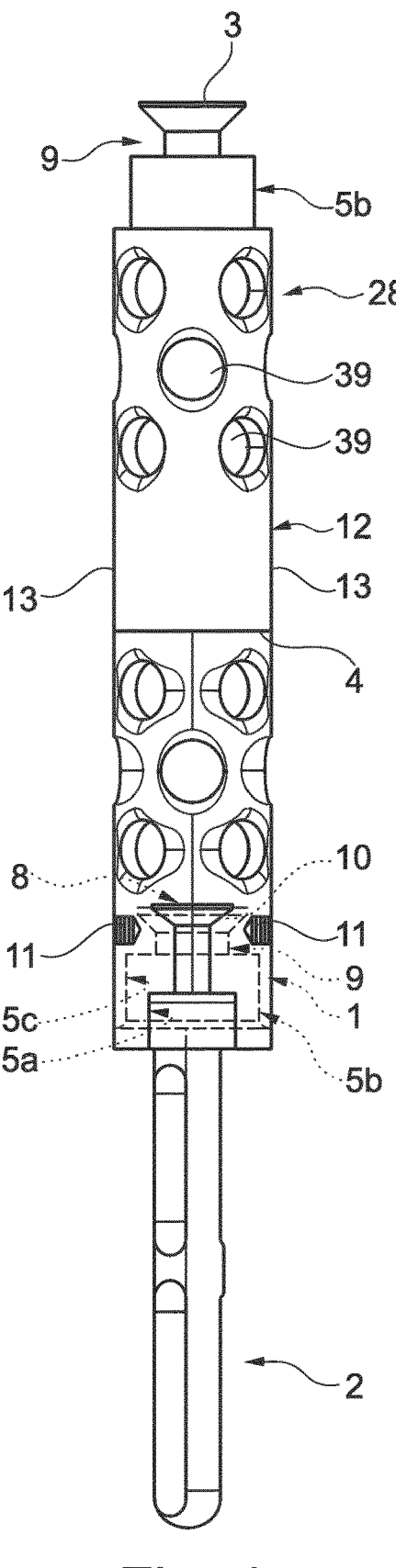
FIG. 4 is a front view of a set, comprising the set of FIG. 2B and another humeral implant component, in an assembled and un-assembled state.

FIG. 4 is a front view of a set. The set comprises the set of FIG. 2B and another humeral implant component 28, wherein the other humeral implant component 28 is shown both in an assembled and un-assembled state. The other humeral implant component may serve as a replacement of a section of a humerus. The other humeral implant component 28 comprises a first end 3 and a second end 4. At the first end 3 of the other humeral implant component 28 there is provided the same interface part 5b and the same circumferential groove 9 as for the humeral implant component 1. In particular, there is provided an axial through hole at the same location as the through hole 7 of the humeral implant component 1. However, the axial through hole of the other implant component 28 is preferably threaded. The other humeral implant component 28 further comprises an elongated body 12 having a cylindrical shape. More specifically, the elongated body 12 has a shape of a hollow cylinder.

The elongated body 12 further comprises holes 39 for receiving an active substance or medication, for example for treating or preventing against an infection. These holes may also serve for attaching soft tissue structures using, for example, sutures.

At the second end of the other humeral implant component 28 there is provided a tapered interface part 5c, which, in this case, is an inner interface part 5c. The inner interface part 5c is configured to engage with the outer interface part 5b of the humeral implant component 1 to form a tapered connection between the other humeral implant component 28 and the humeral implant component 1. In order to lock this tapered connection, transversal holes are provided in the elongated body 12 which are configured to be penetrated by at least one and preferably two transversal fasteners 11, the transversal fastener preferably being a screw. Each transversal fastener 11 is engaged with the tapered groove side wall 10 of the circumferential groove 9. With this configuration, by engaging the transversal fastener 11 with the tapered groove side wall 10 of the humeral implant component 1, the humeral implant component 1 is pulled into the elongated body 12 of the other humeral implant component 28, thereby locking the tapered connection between the two humeral implant components.

Furthermore, since the screw 8 is preferably a countersunk screw, the head of which penetrates the humeral implant component 1, there is no interaction between the screw 8 and the transversal fastener 11, thereby preventing that the transversal fastener 11 loosens the screw 8 when being screwed into the other humeral implant component 28.

Figures 5A, 5B:
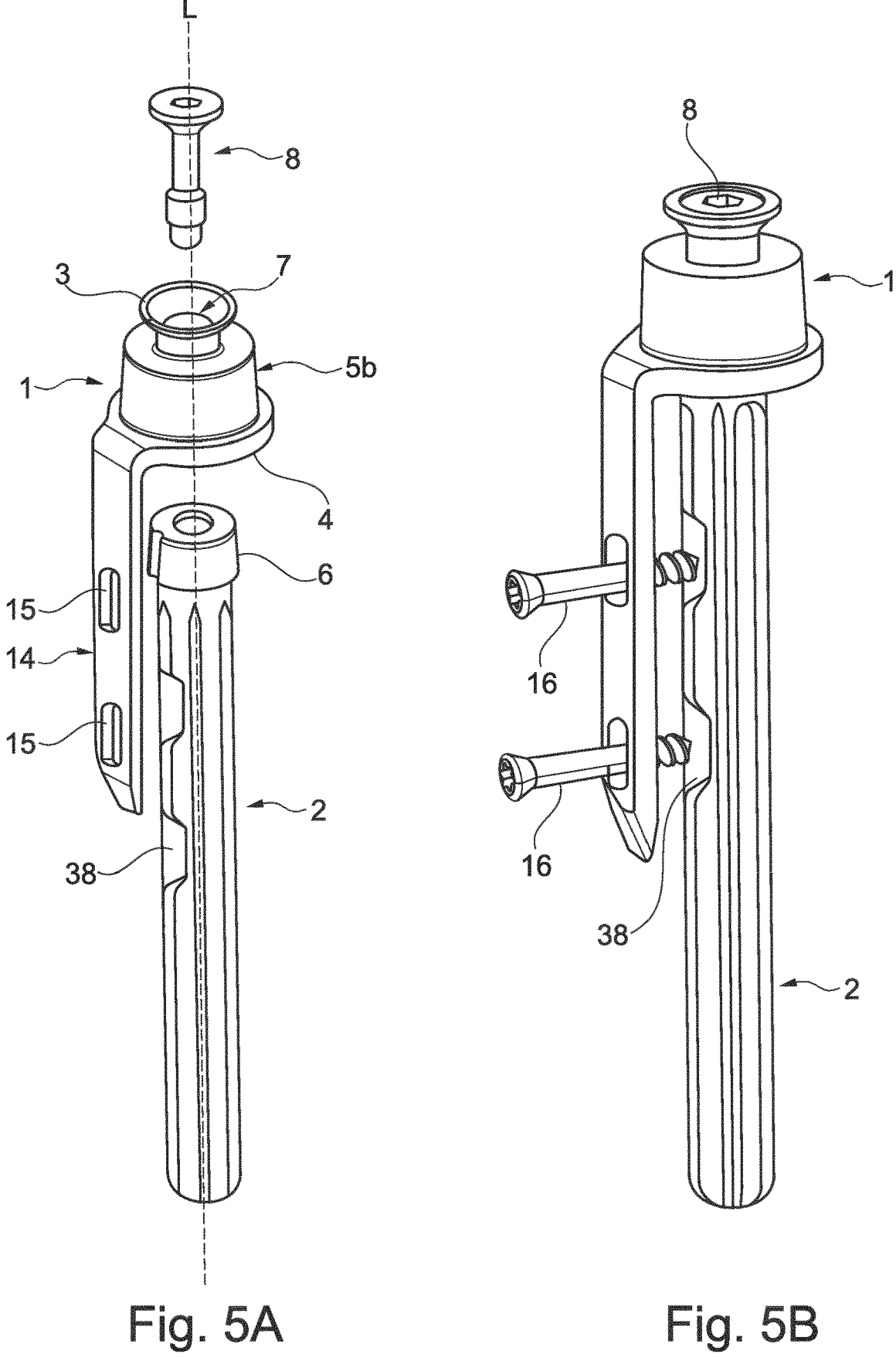
FIG. 5A is a perspective view of a set, comprising a humeral implant component having a plate-shaped portion, in an un-assembled state.
FIG. 5B is a perspective view of the set of FIG. 5A in an assembled state.

FIG. 5A is a perspective view of a set, comprising a humeral implant component 1 having a plate-shaped portion 14, in an un-assembled state. As can be seen, the plate-shaped portion 14 extends substantially parallel to the longitudinal axis L of the humeral implant component 1. The plate-shaped portion 14 extends in a direction from the first end 3 to the second end 4 and away from the second end 4.

In addition, the plate-shaped portion 14 comprises two transversal through holes 15 which, when the humeral implant component 1 forms the tapered connection with the tapered interface part 6 of the other humeral implant component 2, face respective stem holes 38 of the other humeral implant component 2.

As illustrated in FIG. 5A, the humeral implant component 1 is substantially configured like the humeral implant component 1 of FIGS. 1 and 2 except for the plate-shaped portion 14. Accordingly, the humeral implant component allows for a compact build of the assembly. At the same time, the distance of the plate-shaped portion to the longitudinal axis L may be adapted without affecting the remaining assembly. This can be achieved by selecting a component with a predetermined distance to the longitudinal axis.

FIG. 5B is a perspective view of the set of FIG. 5A in an assembled state. As can be seen, fixation means 16 are provided to penetrate through the transversal through holes 15 and the stem holes 38 in order to fixate the set to a bone of a human being.

FIG. 6A is a front view of a set, comprising the humeral implant component 1 of FIG. 1 comprising a second interface part 19 and a second circumferential groove 20, in an un-assembled state. As can be seen, the humeral implant component 1 has a mirror symmetric shape with respect to the base part 35. In this example, the humeral implant component 1 forms a male-male adapter, wherein a threaded through hole 7 is provided at the first end 3 and at the second end 4. In the set shown in FIG. 6A, the humeral implant component 1 can therefore form two tapered connections with two other humeral implant components 28, the two other humeral implant components 28 comprising the elongated body 12. More specifically, the outer interface part 5b engages with the inner interface part 5c and the other interface part 19 engages with the other inner interface part 5c of the other humeral implant component 28. The two tapered connections are respectively locked by means of transversal fasteners 11 penetrating through transversal holes 13 of the other humeral implant component 28.

As illustrated in FIGS. 6A to 6C, the outer interface parts 5b and 19 are basically adjacent to each other so that the humeral implant component can serve as an adapter between the two other humeral implant components, substantially without increasing the length of the assembly.

FIG. 6B is a front view of another set, comprising the humeral implant component 1 of FIG. 6A, in an un-assembled state. In this case, the tapered connection comprising the second interface part 19 is locked by means of the screw 24 provided in the second humeral implant component 40. The screw 24 engages with the corresponding thread of the through hole 7 of the humeral implant component 1 in order to lock the tapered connection. FIG. 6C is a front view of yet another set, comprising the humeral implant component 1 of FIG. 6A, in an un-assembled state. FIGS. 6A to 6C demonstrate the modular flexibility of the humeral implant component 1.

Figure 7:
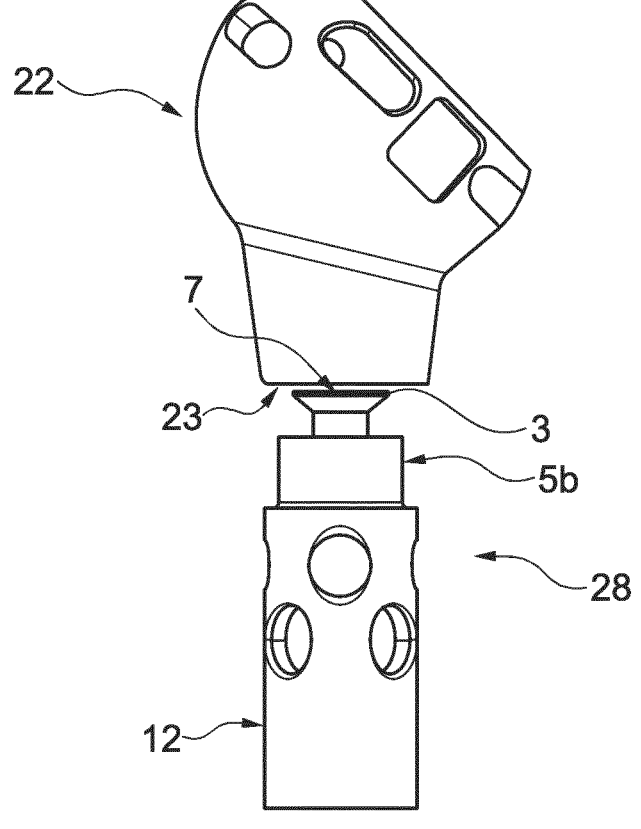
FIG. 7 is a front view of a set, comprising a humeral implant component comprising an elongated body and a second humeral implant component, in an un-assembled state.

FIG. 7 is a front view of a set, comprising a humeral implant component 28 comprising an elongated body 12 and a second humeral implant component 22, in an un-assembled state. The second humeral implant component 22 is a humeral implant body. In this case, the tapered connection between the humeral implant component 28 and the second humeral implant component 22 is formed by engaging the outer interface part 5b of the humeral implant component 28 with the tapered interface part 23 of the second humeral implant component 22. The tapered interface part 23 can be better seen in FIG. 8.

Figure 8:
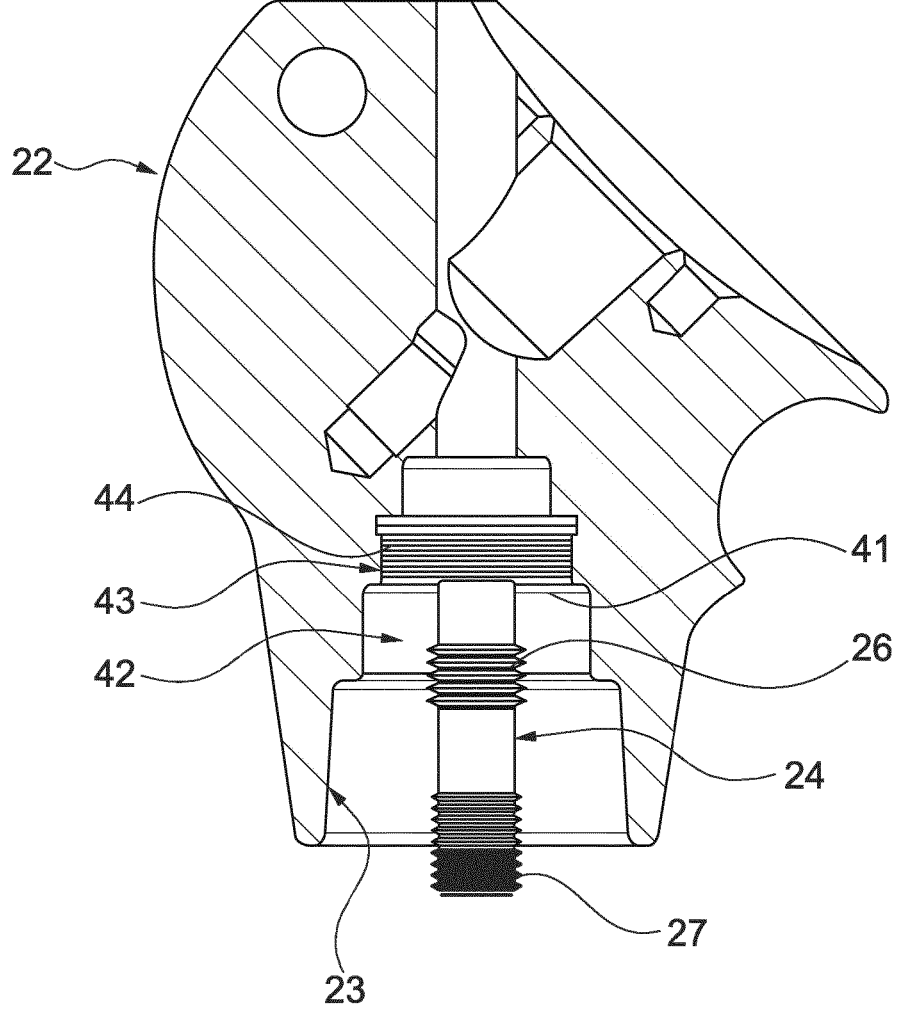
FIG. 8 is a partial cross-sectional front view of the second humeral implant component of the set of FIG. 7, showing a captive screw with two threads.

FIG. 8 is a partial cross-sectional front view of the second humeral implant component 22 of FIG. 7. As can be seen, the tapered interface part 23 forms an inner interface part 23 in a recessed portion 42 of the second humeral implant component 22. When forming the tapered connection between the humeral implant component 28 and the humeral implant component 22, the first end 3 of the humeral implant component 28 abuts at the abutment surface 41 formed in the recessed portion 42 of the second humeral implant component 22.

Also shown in FIG. 8 is the screw 24, which, in this case, is a captive screw 24. The captive screw 24 is provided in the second humeral implant component 22. The captive screw 24 penetrate a ring-shaped body 43, wherein the ring-shaped body 43 comprises an outer thread 44. The outer thread 44 of the ring-shaped body 43 engages an inner thread provided in the recessed portion 42 of the second humeral implant component 22. Accordingly, the ring-shaped body 43 is fixed in the second humeral implant component 22 by forming a threaded engagement with the inner thread of second humeral implant component 22, thereby fixing the captive screw 24 within the second humeral implant component 22. In the set shown in FIG. 7, the tapered connection between the humeral implant component 28 and the second humeral implant component is locked by the captive screw 24, wherein the first thread 26 engages with the threaded through hole 7 of the humeral implant component 28.

Figure 9:
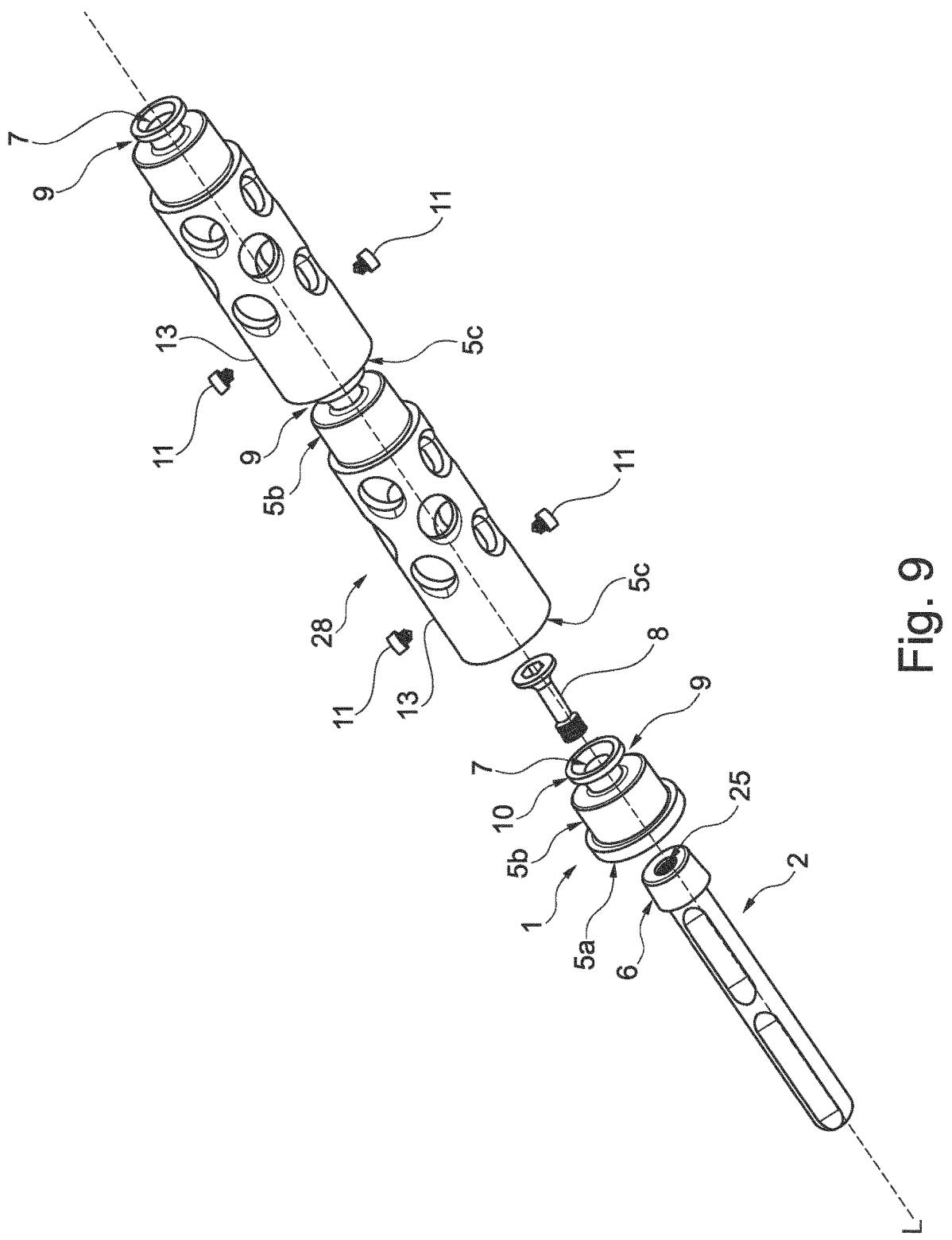
FIG. 9 is a perspective view of a set, comprising the humeral implant component of FIG. 1, another humeral implant component, the longitudinal fastener, and two humeral implant components comprising elongated bodies, in an un-assembled state.

The second thread 27 is configured to engage with a corresponding inner thread of the threaded hole 25 of the stem 2 (the other humeral implant component 2), see FIG. 9.

FIG. 9 is a perspective view of a set, comprising the humeral implant component 1 of FIG. 1, the other humeral implant component 2, the longitudinal fastener 8, and two humeral implant components 28 comprising elongated bodies 12, in an un-assembled state. In the set shown in FIG. 9, three tapered connections are shown. One tapered connection is formed between the stem 2 and the humeral implant component 1. The second tapered connection is formed between the humeral implant component 1 and the other humeral implant component 28. The third tapered connection is formed between the two humeral implant components 28. The tapered connections are either locked by the longitudinal fastener 8 or by the transversal fastener 11. In either case, the tapered connection comprises the advantages described above.

FIG. 10 is a front view of a set, comprising the humeral implant component 1 of FIG. 1, the second humeral implant component 22 of FIG. 7, and the other humeral implant component 2 of FIG. 2A, in an un-assembled state. In this case, the second humeral implant component 22 comprises the captive screw 24 shown in FIG. 8.

Furthermore, in this case, the humeral implant component comprises a through hole 7 which does not comprise a thread. That is, the captive screw 24 comprising the first thread 26 and the second thread 27 is configured to penetrate through the through hole 7 of the humeral implant component 1 without engaging the through hole 7. In this case, the tapered connections, both between the second humeral implant component 22 and the first humeral implant component 1 and the first humeral implant component 1 and the other humeral implant component 2, are locked by the captive screw 24, wherein the second thread 27 engages with the threaded hole 25 of the other humeral implant component 2.

Figure 11:
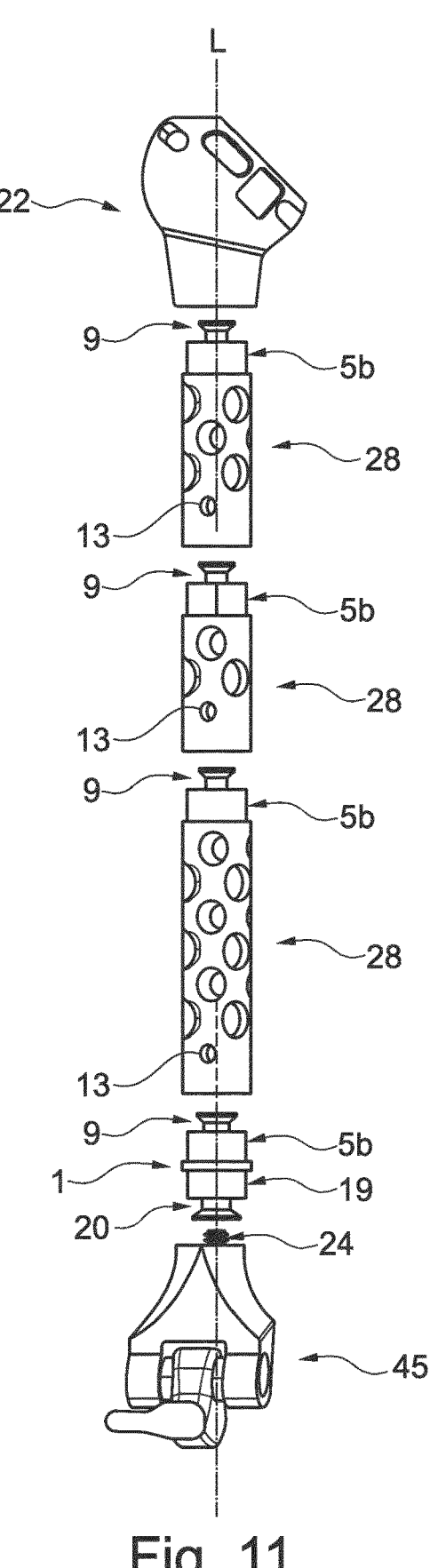
FIG. 11 is a front view of a set, comprising the humeral implant component of FIGS. 6A to 6C, three humeral implant components comprising elongated bodies, the second humeral implant component of FIG. 7, and an elbow implant component, in an un-assembled state.

FIG. 11 is a front view of a set, comprising the humeral implant component 1 of FIGS. 6A to 6C, three humeral implant components 28 comprising elongated bodies 12, the second humeral implant component 22 of FIG. 7, and an elbow implant component 45, in an un-assembled state. Although not shown in FIG. 11, the tapered connections between the humeral implant components 28 as well as the tapered connection between the humeral implant component 28 and the humeral implant component 1 are locked by the transversal fastener 11 penetrating through respective transversal holes 13.

Furthermore, as can be seen in FIG. 11, the elongated bodies 12 of the humeral implant component 28 have different lengths along the longitudinal axis L. With this configuration, due to the modular flexibility of the humeral implant components, a customized implant device can be provided.

Figure 12A:
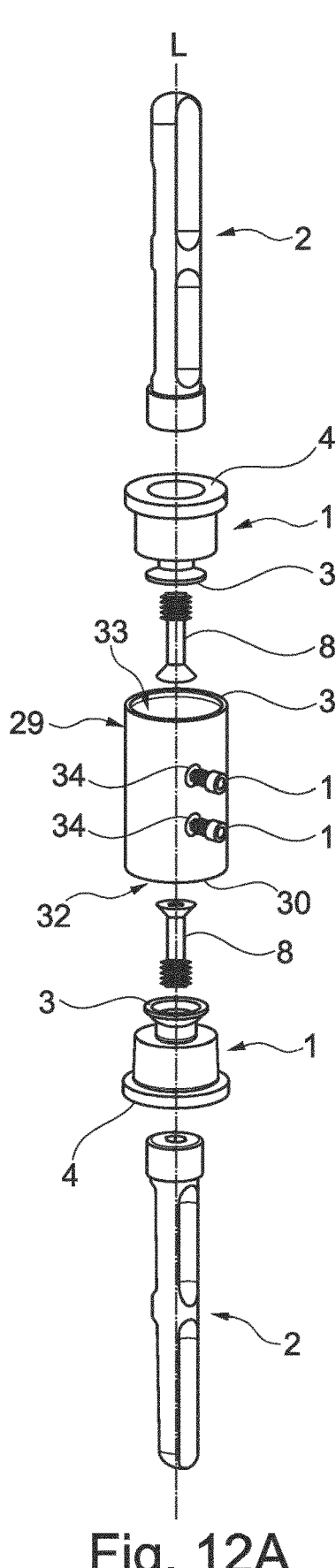
FIG. 12A is a perspective front view of a set, comprising two sets of FIG. 2A and a third humeral implant component, in an un-assembled state.

FIG. 12A is a perspective front view of a set, comprising two sets of FIG. 2A and a third humeral implant component 29, in an un-assembled state.

The third humeral implant component 29 has the shape of a hollow cylinder. In the example shown, the third humeral implant component 29 has a first end 30 and a second end 31 opposing each other along the longitudinal axis L of the third humeral implant component 29. The third humeral implant component 29 further comprises a first end tapered interface part 32 and a second end tapered interface part 33. The first end tapered interface part 32 is provided at the first end 30 and the second end tapered interface part 33 is provided at the second end 31. Both the first end tapered interface part 32 and the second end tapered interface part 33 form inner interface parts. Furthermore, the third humeral implant component 29 comprises transversal holes 34 for receiving transversal fasteners 11.

Figure 12B:
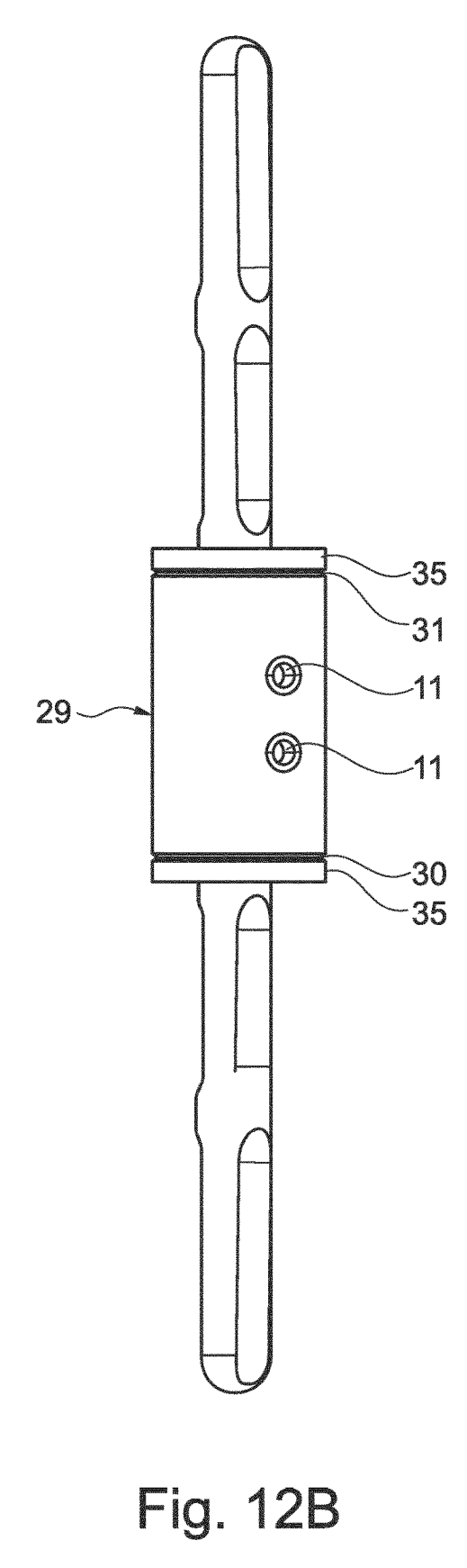
FIG. 12B is a front view of the set of FIG. 12A in an assembled state.

FIG. 12B is a front view of the set of FIG. 12A in an assembled state. As can be seen, tapered connections between the humeral implant components 1 and the third humeral implant component 29 are formed such that the base part 35 of the humeral implant component 1 abuts at one of the first end 30 and the second end 31 of the third humeral implant component 29. The set shown in FIG. 12B may be applied to the humerus of a human being.

Figures 13A, 13B:
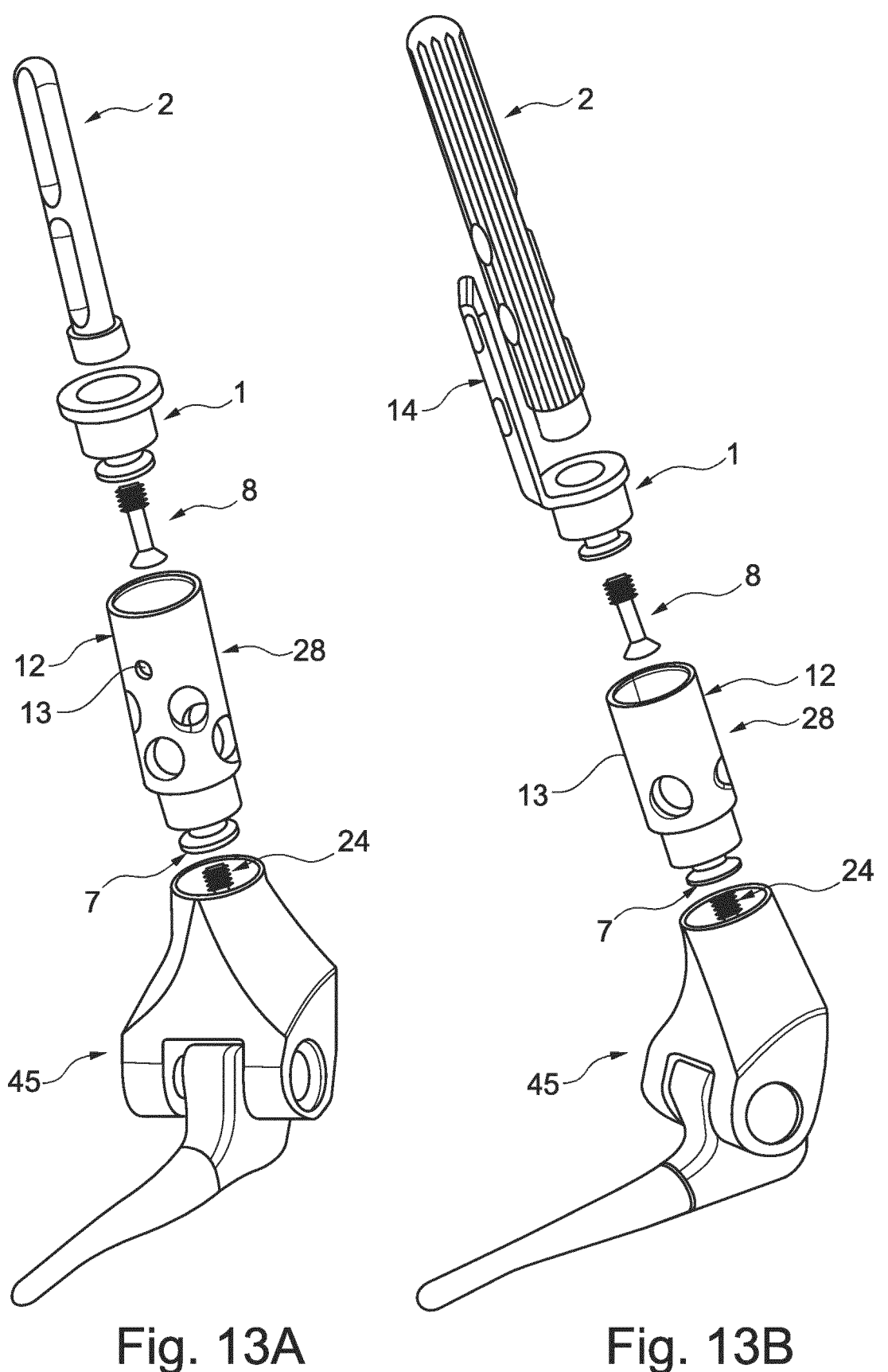
FIG. 13A is a perspective view of a set, comprising the set of FIG. 2A, another humeral implant component comprising an elongated body, and the elbow implant component of FIG. 11, in an un-assembled state.
FIG. 13B is a perspective view of a set, comprising the set of FIG. 5A, another humeral implant component comprising an elongated body, and the elbow implant component of FIG. 11, in an un-assembled state.

FIG. 13A is a perspective view of a set, comprising the set of FIG. 2A, another humeral implant component 28 comprising an elongated body 12, and the elbow implant component 45 of FIG. 11, in an un-assembled state.

FIG. 13B is a perspective view of a set, comprising the set of FIG. 5A, another humeral implant component 28 comprising an elongated body 12, and the elbow implant component 45 of FIG. 11, in an un-assembled state.

Next, a method for assembling an implant device will be described with respect to FIG. 9. The method described in this context is applicable in a corresponding way to the other sets of this disclosure.

In the first step, the humeral implant component 1 and the other humeral implant component 2 are linearly pre-arranged one after another along the longitudinal axis L. In the second step, the humeral implant component 1 and the other humeral implant component 2 are moved towards each other, thereby forming the tapered connection between the humeral implant component 1 and the other humeral implant component 2. More specifically, the tapered connection is formed by forming a tapered engagement between the tapered interface part 6 of the other humeral implant component 2 and the inner interface part 5a of the humeral implant component 1. In the third step, the tapered connection between the humeral implant component 1 and the other humeral implant component 2 formed in the second step is locked by forming a threaded engagement between the screw 8 and the threaded hole 25 of the other humeral implant component 2.

In the fourth step, the humeral implant component 28 is moved towards the humeral implant component 1, thereby forming the tapered connection between the outer interface part 5b of the humeral implant component 1 and the inner interface part 5c of the humeral implant component 28. In the fifth step, the tapered connection formed between the humeral implant component 1 and the humeral implant component 28 is locked by engaging the tapered groove side wall 10 of the circumferential groove 9 of the humeral implant component 1 with the transversal fastener 11 penetrating through the transversal holes 13 of the humeral implant component 28.

In the sixth step, the other humeral implant component is connected to the humeral implant component 28 as described in the fourth and fifth steps.

A skilled person will readily appreciate that the order of forming tapered connections can also be interchanged. For example, the tapered connection between the two humeral implant components 28 may be formed first, before forming the tapered connection between the other humeral implant component 2 and the humeral implant component 1.

LIST OF REFERENCE SIGNS

1 humeral implant component
2 stem (other humeral implant component)
3 first end (of the humeral implant component)
4 second end (of the humeral implant component)
5a inner interface part (interface part)

5b outer interface part (interface part)
5c inner interface part, tapered interface part
6 tapered interface part (of the other humeral implant component)
7 through hole
8 screw (longitudinal fastener)
9 circumferential groove
10 tapered groove side wall
11 transversal fastener
12 elongated body
13 transversal hole
14 plate-shaped portion
15 transversal through hole
16 fixation means
19 second interface part
20 second circumferential groove
21 second tapered groove side wall
22 second humeral implant component
23 tapered interface part (of the second humeral implant component)
24 screw (with first thread 26 and second thread 27)
25 threaded hole
26 first thread
27 second thread
28 humeral implant component, other humeral implant component, third humeral implant component
29 third humeral implant component
30 first end (of the third humeral implant component)
31 second end (of the third humeral implant component)
32 first end tapered interface part
33 second end tapered interface part
34 transversal hole (of the third humeral implant component)
L longitudinal axis (of the humeral implant component)
35 base part
36 other groove side wall (of the circumferential groove)
37 thread (of the longitudinal fastener)
38 stem hole
39 hole (of the elongated body)
40 second humeral implant component
41 abutment surface
42 recessed portion
43 ring-shaped body
44 thread (of the ring-shaped body)
45 elbow implant component

The invention claimed is:

1. A humeral implant component connectable to another humeral implant component, the humeral implant component comprising:

a longitudinal axis;

a first end and a second end, the first end and the second end opposing each other along the longitudinal axis of the humeral implant component;

a first interface part for connecting the humeral implant component to the other humeral implant component, wherein the first interface part is tapered along the longitudinal axis in a direction from the second end to the first end, the first interface part being engageable with a tapered interface part of the other humeral implant component to form a first tapered connection between the humeral implant component and the other humeral implant component, wherein the humeral implant component further comprises a through hole extending along the longitudinal axis for locking the first tapered connection by a longitudinal fastener;

a second interface part configured to connect the humeral implant component to the another humeral implant component via a second tapered connection; and a circumferential groove comprising a tapered groove side wall, wherein the tapered groove side wall is tapered along the longitudinal axis in a direction from the first end to the second end, and wherein the tapered groove side wall is engageable with at least one transversal fastener for locking the other tapered connection.

2. The humeral implant component of claim 1, wherein the through hole comprises a thread for a threaded engagement with the longitudinal fastener.

3. The humeral implant component of claim 1, wherein the first interface part is an inner interface part.

4. The humeral implant component of claim 3, wherein the inner interface part is provided at the second end.

5. The humeral implant component of claim 3, further comprising:

At least a second interface part, for connecting the humeral implant component to another humeral implant component via a tapered connection, wherein the at least second interface part is the inner interface part and the outer interface part.

6. The humeral implant component of claim 5, further comprising:

a circumferential groove comprising a tapered groove side wall, wherein the tapered groove side wall is tapered along the longitudinal axis in a direction from the first end to the second end, and wherein the tapered groove side wall is engageable with at least one transversal fastener, for locking the other tapered connection.

7. The humeral implant component of claim 6, further comprising:

an elongated body, the elongated body being positioned between the first end and the second end, wherein the elongated body comprises at least one transversal hole for mating with transversal fasteners and locking the other tapered connection, and further comprising:

a plate-shaped portion, the plate shaped portion being attached to and integrally formed with the second end and extending away from the second end parallel to the longitudinal axis in a direction from the first to the second end, wherein the plate shaped portion comprises at least one transversal through hole.

8. A set, comprising:

the humeral implant component of claim 5, a second humeral implant component, wherein the second humeral implant component comprises a second humeral implant component tapered interface part at one end thereof, wherein the interface part of the humeral implant component is configured to engage with the second humeral implant component tapered interface part to form a second humeral implant component tapered connection between the humeral implant component and the second humeral implant component, the second humeral implant component extending from the one end of the second humeral implant component into the second humeral implant component, a third humeral implant component, wherein the third humeral implant component comprises a third humeral implant component tapered interface part at one end thereof, wherein the other interface part of the humeral implant component is configured to engage with the third humeral implant component tapered interface part to form a third humeral implant component tapered connection between the humeral implant component and the third humeral implant component, and a screw, the screw being provided in the third humeral implant component, wherein the screw is configured to lock the third humeral implant component tapered connection and the second humeral implant component tapered connection by forming a threaded engagement with the threaded hole of the second humeral implant component.

9. The humeral implant component of claim 1, wherein the interface part forms a conical taper or wherein the other interface part forms a conical taper.

10. The humeral implant component of claim 1, further comprising:

a second interface part for connecting the humeral implant component to the other humeral implant component, wherein the second interface part is tapered along the longitudinal axis in a direction from the first end to the second end, the second interface part being engageable with the tapered interface part of the other humeral implant component to form the tapered connection between the humeral implant component and the other humeral implant component.

11. The humeral implant component of claim 10, further comprising:

a second circumferential groove comprising a second tapered groove side wall, wherein the second tapered groove side wall is tapered along the longitudinal axis in a direction from the second to the first end, wherein the second tapered groove side wall is engageable with at least one transversal fastener.

12. A set, the set comprising:

the humeral implant component of claim 11, a second humeral implant component, wherein the second humeral implant component comprises a tapered interface part at one end thereof, wherein the interface part of the humeral implant component is configured to engage with the tapered interface part of the second humeral implant component to form a tapered connection between the humeral implant component and the second humeral implant component, and a screw, the screw being provided in the second humeral implant component, wherein the screw is arranged to lock the tapered connection by forming a threaded engagement with the through hole of the humeral implant component.

13. The set of claim 12, wherein the screw comprises a first thread and a second thread, the first thread being different from the second thread, wherein the first thread and the second thread are arranged separately along a longitudinal screw axis of the screw, wherein the first thread is configured to form a threaded engagement with the through hole of the humeral implant component and the second thread is configured to form a threaded engagement with the threaded hole of the second humeral implant component.

14. A set, the set comprising:

the humeral implant component of claim 1, a second humeral implant component, wherein the second humeral implant component comprises a tapered interface part at one end thereof, wherein the interface part of the humeral implant component is configured to engage with the tapered interface part of the second humeral implant component to form a tapered connection between the humeral implant component and the second humeral implant component, the second humeral implant component further comprising a threaded hole extending from the one end of the second humeral implant component into the second humeral implant component, and a screw, wherein the screw is configured to penetrate the through hole of the humeral implant component and to lock the tapered connection by engaging the threaded hole.

15. The set of claim 14, wherein the humeral implant component is a first humeral implant component, the set further comprising:

a third humeral implant component, the third humeral implant component, the third humeral implant component forming another tapered connection with the other interface part of the first humeral implant component, and at least one transversal fastener, said at least one transversal fastener being configured to penetrate a transversal hole of the third humeral implant component for locking the other tapered connection by engaging with the tapered groove side wall of the first humeral implant component, wherein the third humeral implant component preferably comprises at least two transversal holes.

16. A set, comprising:

two of the sets of claim 14, a third humeral implant component, the third humeral implant component comprising a longitudinal axis, a first end and a second end, the first end and the second end opposing each other along the longitudinal axis of the third humeral implant component, a first end tapered interface part and a second end tapered interface part, the first end tapered interface part being located at the first end and the second end tapered interface part being located at the second end of the third humeral implant component, wherein the first end tapered interface part is tapered along the longitudinal axis of the third humeral implant component in a direction from the first to the second end of the third humeral implant component and the second end tapered interface part is tapered in a direction opposite to the first end tapered interface part, at least one transversal hole, arranged between the first end and the second end of the third humeral implant component, non-equidistant from the first and the second end of the third humeral implant component, at least one transversal fastener configured to penetrate the at least one transversal hole, wherein one of the two sets is configured to form a tapered connection at the first end of the third humeral implant component and the other one of the two sets is configured to form a tapered connection at the second end of the third humeral implant component, wherein one of the first and second ends of the humeral implant components of the two sets face each other and the other one of the first and second ends of the humeral implant components of the two sets face away from each other when forming tapered connections with the third humeral implant component, wherein the tapered connections are locked by the transversal fastener engaging with the respective tapered groove side wall of the humeral implant components.

17. A set, comprising:

at least two of the humeral implant components of claim 1, wherein one of the humeral implant components is configured to form a tapered connection with the other one of the humeral implant components, and wherein the tapered connection is locked by the at least one transversal fastener.

* * * * *